(12) United States Patent
Bondestam

(10) Patent No.: US 6,779,378 B2
(45) Date of Patent: Aug. 24, 2004

(54) METHOD OF MONITORING EVAPORATION RATE OF SOURCE MATERIAL IN A CONTAINER

(75) Inventor: Niklas Bondestam, Helsinki (FI)

(73) Assignee: ASM International N.V., Bilthoven (NL)

( * ) Notice: Subject to any disclaimer, the term of this patent is extended or adjusted under 35 U.S.C. 154(b) by 0 days.

(21) Appl. No.: 10/285,348

(22) Filed: Oct. 30, 2002

(65) Prior Publication Data

US 2004/0083787 A1 May 6, 2004

(51) Int. Cl.[7] .................................................. G01N 7/14
(52) U.S. Cl. .................... 73/19.05; 73/64.45; 73/64.46
(58) Field of Search ............................ 73/19.05, 61.77, 73/64.45, 64.46

(56) References Cited

U.S. PATENT DOCUMENTS

| | | | |
|---|---|---|---|
| 3,731,523 A | * | 5/1973 | Vissers et al. ............. 73/19.05 |
| 4,357,824 A | * | 11/1982 | Foss et al. ................. 73/19.05 |
| 4,393,013 A | | 7/1983 | McMenamin |
| 4,436,674 A | | 3/1984 | McMenamin |
| 4,553,431 A | | 11/1985 | Nicolai |
| 4,840,064 A | | 6/1989 | Fudim |
| 5,001,924 A | | 3/1991 | Walter et al. |
| 5,535,624 A | | 7/1996 | Lehmann |
| 5,760,294 A | | 6/1998 | Lehmann |
| 5,810,058 A | | 9/1998 | Kountz et al. |
| 6,038,919 A | | 3/2000 | Schmitt et al. |

* cited by examiner

*Primary Examiner*—Daniel S. Larkin
(74) *Attorney, Agent, or Firm*—Knobbe, Martens, Olson & Bear, LLP.

(57) ABSTRACT

A method for monitoring the capability of a source container comprising liquid or solid source material to produce vaporized source material comprises extracting vaporized source material from the source container. The source container is then isolated and a property indicative of the partial pressure of the vaporized source material is then measured as a function of time. The partial pressure (or property indicative thereof) as a function of time is compared with a reference partial pressure as a function of time. An alarm is generated when the difference between the measured property (indicative of partial pressure) as a function of time and the reference property value as a function of time is larger than a predetermined property difference limit. The property can be, for example, overall pressure or source material concentration in the gas phase.

19 Claims, 4 Drawing Sheets

METHOD OF MONITORING EVAPORATION RATE OF SOURCE MATERIAL IN A CONTAINER

FIELD OF THE INVENTION

The invention relates to a chemical processing system that uses a vaporized liquid or solid source material. More particularly, the invention relates to a vapor deposition system that uses a vaporized liquid or solid source material.

BACKGROUND OF THE INVENTION

Liquid or solid source materials are used in many chemical processing systems, such as, for example, Chemical Vapor Deposition (CVD) processes. The liquid or solid source material is typically vaporized in a source container. In a CVD process, the vapor is fed to a reaction chamber in which the vaporized source material is subjected to a chemical reaction and a film is deposited onto a substrate. To ensure that an adequate and constant amount of vapor is delivered to the reaction chamber, it is desirable to monitor the vaporization process in the source container.

U.S. Pat. No. 4,436,674 discloses a vapor mass flow control system wherein a controlled amount of carrier gas is bubbled through a liquid source material in a source container of known temperature and pressure and the level of the liquid source material is sensed. In this system, it is assumed that under constant conditions a constant degree of saturation of the carrier gas with reactant vapor is achieved. As such, when the level of the reactant in the source container decreases, the degree of saturation will decrease. It is therefore important to be able to sense the level of the source material and to control the level of source material within a certain range.

In case of highly reactive source materials, such as those as used in Metal Organic CVD (MOCVD) or Atomic Layer Deposition (ALD), sensing the level of the reactant may be difficult because the source container is made of a robust metal. In addition, it is generally not desirable to place level sensing devices inside the source container as they may be damaged by the reactive source materials. Further, in the case of solid source materials, it is particularly difficult to sense the level or amount of source material in the source container.

A method to measure the amount of reactant in a source container without a level sensor is disclosed by U.S. Pat. No. 6,038,919 to Schmitt et al. In the method disclosed by Schmitt et al, a source container with a known volume is isolated. A known amount of inert gas is then fed into the source container. The temperature of the source container is monitored while the pressure rise due to the gas supply is measured. The free volume of the gas in the source container is calculated using the gas law of Boyle-Gay-Lussac. By subtracting the free volume of gas from the total inner volume of the source container, the volume of the solid or liquid material can be determined.

However, the method of Schmitt et al. has several disadvantages. For example, solid source materials have a tendency to develop a crust on the outer surface that hampers vaporization. That is, although sufficient material might be present in the source container and detected by the Schmitt et al. procedure, the condition of the material is such that not enough vapor is produced. Also in the case of liquid source material, contamination might float on the top surface of the liquid, which can also hamper the vaporization.

SUMMARY OF THE INVENTION

Therefore, there is not only a need to measure the amount of liquid or solid source material but also a need to monitor the capability of the source material in the source container to deliver vaporized source material.

Accordingly, one aspect of the present invention is a method to monitor the capability of a source container comprising liquid or solid source material to produce vaporized source material. In one embodiment, the method comprises the steps of: extracting vaporized source material from the source container, thereby reducing the amount of vaporized source material in the source container, isolating the source container; measuring a property that is indicative of a partial pressure of the vaporized source material in the source container as a function of time; comparing the measured property as a function of time with a reference property as a function of time; and generating a signal when the difference between the measured property as a function of time and the reference property as a function of time is larger than a predetermined value.

DETAILED DESCRIPTION OF THE PREFERRED EMBODIMENT

Figure 1:
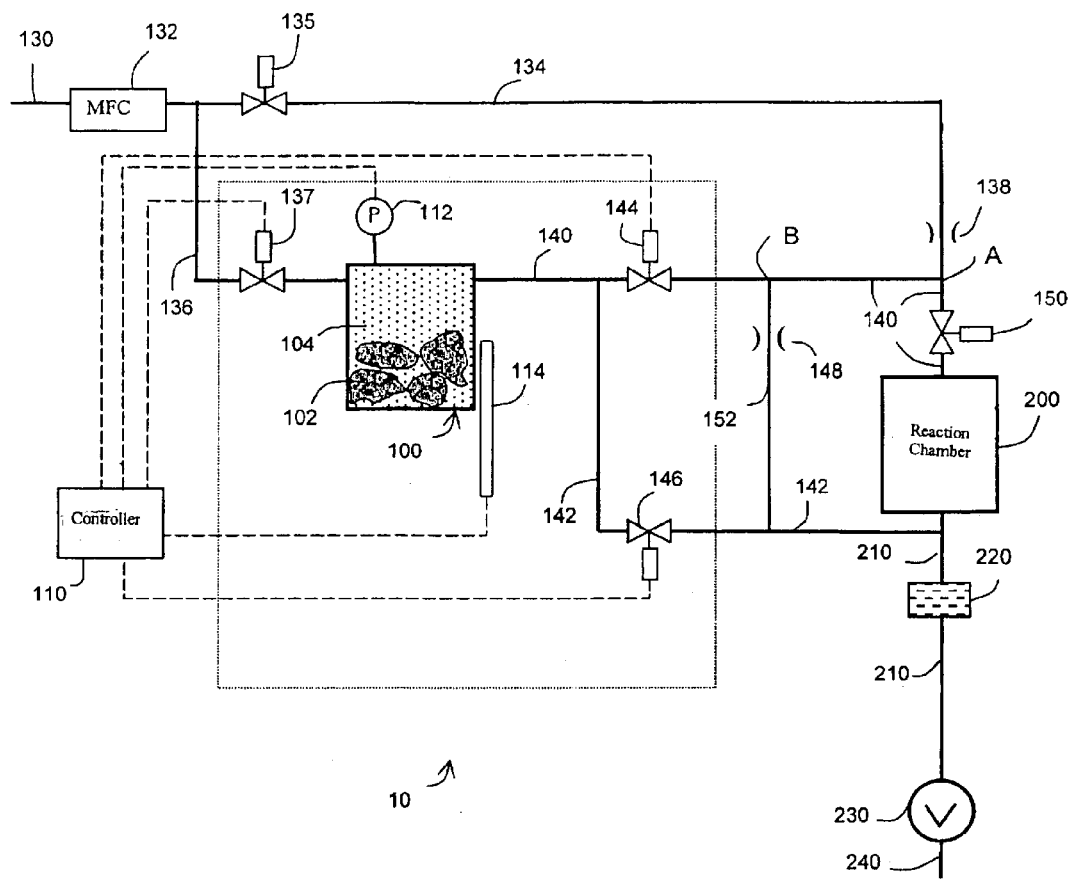
FIG. 1 is a schematic representation of a processing system having certain features and advantages according to an illustrated embodiment of the invention.
Figure 2:
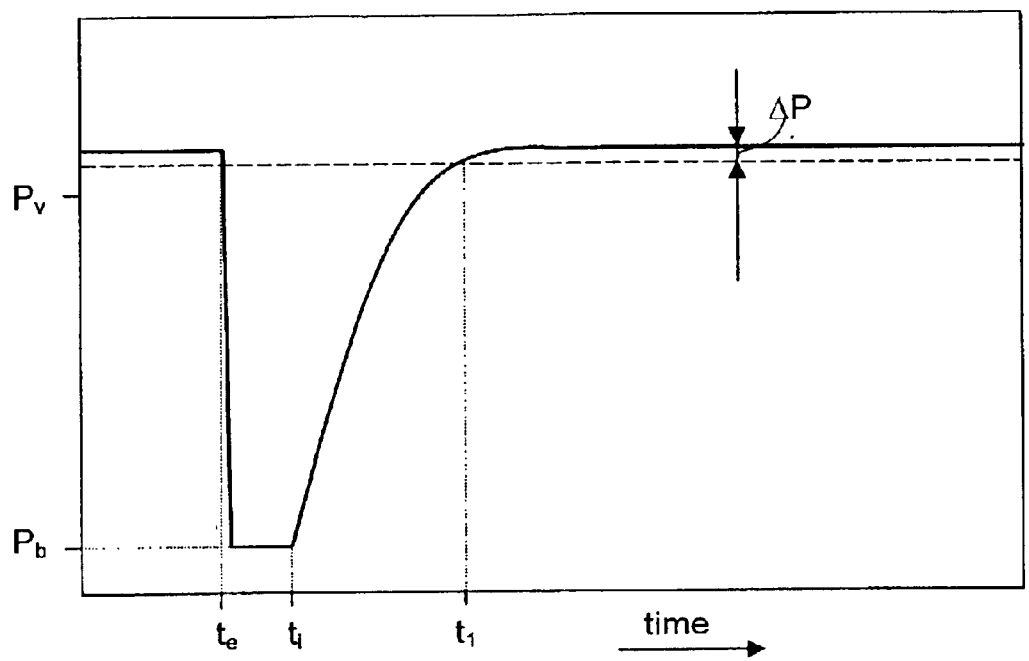
FIG. 2 is a pressure-time curve that illustrates a first arrangement for characterizing the partial pressure recovery of a source material in the source container.

FIG. 1 illustrates a processing system 10 having certain features and advantages according to an illustrated embodiment of the invention.

In the illustrated arrangement, the processing system 10 comprises a source container 100 that is partially filled with solid source material 102. It should be appreciated, however, that certain features and aspects of the illustrated arrangement may also be applicable to liquid source material. Vaporized source material 104 is collected in the upper part of the source container 100.

A temperature sensor 114 is provided for sensing the temperature of the source container 100. Preferably, the source container 100 is heated by a source container heater (not shown) and its temperature is actively controlled at a constant value. The system 10 includes a source container sensor 112 that is in communication with the source container 100. The source container sensor 112 is preferably arranged to measure a property that is indicative of the partial pressure of the vaporized source material 104 in the source container 100. For example, in one arrangement, the source container sensor 112 is a pressure sensor. In a modified arrangement, the source container sensor 112 is a concentration sensor.

The vaporized reactant 104 may be fed to a reaction chamber 200 through a vaporized reactant feed conduit 140 that is provided with first and second isolation valves 144, 150. The reaction chamber 200 is connected via a pump conduit 210 to a vacuum pump 230. The pump conduit 210 is provided with a filter 220. The gases removed by the pump 230 are exhausted through an exhaust conduit 240. In the illustrated arrangement, the source container 100 may be evacuated either through the vaporized reactant conduit 140 and the reaction chamber 200 or through a source container evacuation conduit 142 that is provided with an evacuation valve 146.

As shown in FIG. 1, inert gas is supplied to the source container 100 through an inert gas source line 130, a mass flow controller 132 and an inert gas conduit 136. A controller 110 is provided for controlling an inert gas supply valve 137, which is placed in the inert gas conduit 136 to open and shut the supply of inert gas to the source container 100. Inert gas can also be directed to the reaction chamber 200 via a supply conduit 134 by opening a supply valve 135 positioned in the supply conduit 134. The illustrated processing system 10 also includes a first restriction 138 that is positioned in the supply conduit 134 and a bypass conduit 152, which includes a second restriction 148. In the illustrated arrangement, the container sensor 112, the temperature sensor 114 and the valves 137, 144, 146 in the inert gas, the vaporized reactant and the evacuation conduits 136, 140, 142 are operatively connected to the controller 110. The supply valve 135 and second isolation valve 150 may also be operatively connected to the controller 110.

The bypass conduit 152 and first and second restrictions 138, 148 form an "inert gas valving" system that is described in more detail in U.S. Patent Application Publication U.S. 2001/0054377, which is hereby incorporated by reference herein. It should be appreciated, however, that several features and advantages of the invention can be achieved in a processing system that does not utilize an "inert gas valving" system or utilizes a modified "inert, gas valving" system. The illustrated valving system is preferred when the processing system 10 is arranged for Atomic Layer Deposition (ALD).

The controller 110 preferably comprises a general purpose computer or workstation having a general purpose processor and a memory for storing a computer program that can be configured for performing the steps and functions described herein. In the alternative, the unit may comprise a hard wired feedback control circuit, a dedicated processor, combinations thereof or any other control device that can be constructed for performing the steps and functions described herein.

An apparatus and method for monitoring the capability of the source material to deliver vaporized source material will now be described with continued reference to FIG. 1. In a first arrangement, the source container 100 is evacuated to a base pressure, isolated, and then the recovery of the partial pressure of vaporized source material in the source container 100 is monitored by measuring a property indicative of the partial pressure as a function of time. As applied to the illustrated processing system 10, the property that is indicative of the partial pressure is the total pressure within the source container 100. As such, the illustrated source container sensor 112 is configured as a pressure sensor. The controller 110 is programmed to evacuate the source container 100 during a certain amount of time, preferably by opening the evacuation valve 146 (which is in communication with the pump 230) while the first isolation valve 144 and inert gas supply valve 137 are closed. After the source container 100 is evacuated, the evacuation valve 146 is closed and the source container 100 is left isolated for a time period, while the controller 110 is configured to monitor the pressure recovery as a function of time with use of the pressure sensor 112. The monitored pressure as a function of time is then compared to a reference pressure as a function of time by the controller 110.

The pressure rise as a function of time after evacuating and isolating the source container 100 can be analyzed in several ways. For example, in one arrangement, the equilibrium vapor pressure, corresponding to the temperature at which the source container 100 and the material 102 contained in it is maintained, can be taken as the target value for the pressure. The time required to achieve this equilibrium vapor pressure within certain limits after evacuating and isolating the source container 100 can be registered. If this time deviates beyond a predetermined range from a previously registered time, the controller 100 may generate a signal. In a modified arrangement, the pressure can be measured after a predetermined time elapse after evacuating and isolating the source container 100. If the measured, pressure is less than a predetermined value, the alarm can be generated. In another variation, the pressure rise during a certain time interval can be taken as the parameter to be compared with a previously recorded pressure rise during such a time interval. An advantage associated with using pressure rise is that an offset in the pressure sensor does not affect the calculation.

The signal may be used in several different ways to enhance the operation of the processing system 10. For example, in one embodiment, the signal is an alarm, which may be used to indicate to an operator that the source container 100 needs to be refilled or changed. In another embodiment, the signal may be used to initiate an automatic shut down of the processing system 10 such that the source container 100 can be refilled or changed. In yet another embodiment, the signal may be used to initiate an automatic refill of the source container 100. Of course, those of skill in the art will recognize several other uses for the signal.

The characterization of the pressure recovery as a function of time is described in further detail with reference to FIGS. 2, 3, 4 and 5, which all show the pressure sensed by pressure sensor 112 as a function of time. As indicted in each figure, at $t_e$, the source container 100 is evacuated. Upon evacuation, the pressure rapidly decreases from the vapor pressure $P_v$ to a base pressure $P_b$. The base pressure $P_b$ is determined by the production rate of vaporized source material 104 in the source container 100 and the effective pump capacity available to evacuate the source container 100. It should be noted that the base pressure itself may be used as a measure for the capability of the source container 100 to produce vaporized source material. However, as compared to the methods described above, it is not as advantageous to use because it $P_v$ is particularly sensitive to changes in effective pump capacity and small offsets in the pressure sensor 112.

After some time of evacuation the source container 100 is isolated at an isolation time $t_i$. In the time after the isolation time $t_1$, the pressure in the source container 100 recovers as the free space in the source container 100 is filled with vaporized source material until the pressure reaches the vapor pressure $P_v$, which is the vapor pressure of the source material 102 corresponding to the temperature at which the source container 100 is maintained.

The recovery of the pressure may be characterized in several ways to determine the amount of source material in the source container 100 and the capability of the source material to deliver vaporized source material. For example, in FIG. 2, a recovery time $t_1$ is determined when the pressure in the source container 100 is within a defined range $\Delta P$ of the desired pressure $P_v$. A recovery period $(t_1-t_i)$ is defined as the time period between the isolation time $t_i$ and the recovery time $t_1$. In a preferred arrangement, the recovery period $(t_1-t_i)$ is determined under a reference condition, in which a source container in good operating condition is filled with a new source material and is subjected to the evacuation and isolation steps described above. A reference recovery period $(t_1-t_i)_{ref}$ is therefore obtained and, in one embodiment, is stored in the memory of the controller 110 to be used for future reference. When the processing system 10 is in use, the recovery period $(t_1-t_i)$ is preferably calculated at repeated routine intervals (e.g. at the end of every processing run). In a modified arrangement, the recovery period $(t_1-t_i)$ is calculated at fixed time intervals (e.g., if the system is available, once per day). In either arrangement, the measured recovery period $(t_1-t_i)_{meas}$ is compared with the reference recovery period $(t_1-t_i)_{ref}$ and if the difference between the measured recovery period and the reference recovery period (i.e., $(t_1-t_i)_{ref}-(t_1-t_i)_{meas}$) is larger than a predefined limit, a signal (e.g., an alarm or automatic shutdown or refill signal) may be generated by the controller 110 so that appropriate remedial steps can be taken.

Figure 3:
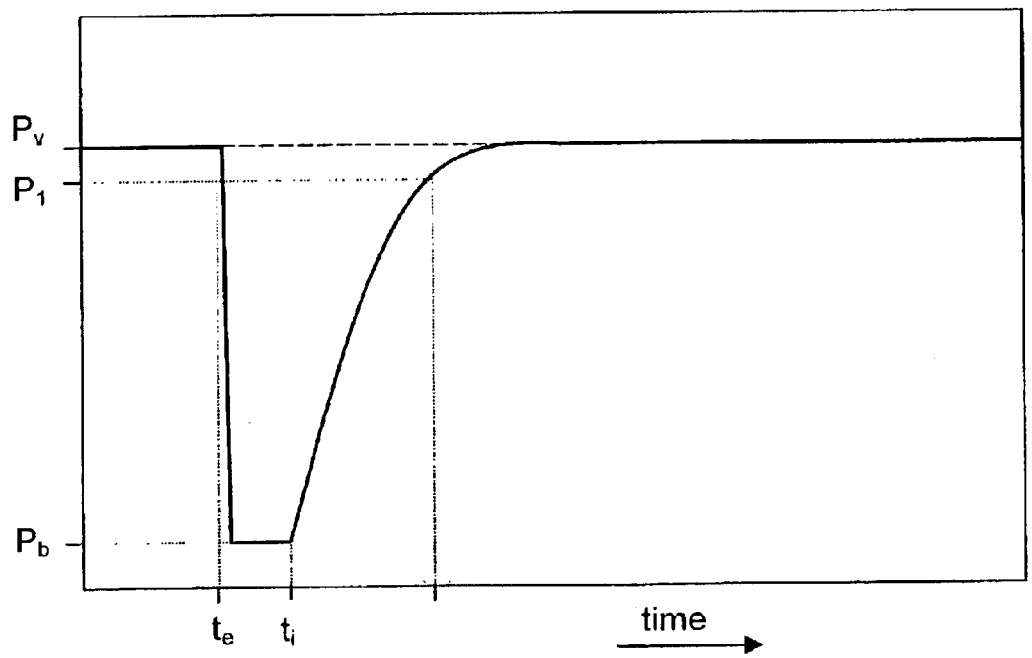
FIG. 3 is a pressure-time curve that illustrates a second arrangement for characterizing the partial pressure recovery of the source material in the source container.

FIG. 3 illustrates a modified arrangement for characterizing the pressure recovery. In this arrangement, the recovery time $t_1$ is an arbitrarily selected predefined time period after the isolation time $t_i$. At the recovery time $t_1$, the pressure is measured to determine a recovery pressure $P_1$. In a manner similar to the previous arrangement, the recovery pressure $P_1$ is preferably determined for a freshly refilled reference source container resulting in a reference recovery pressure $P_{1, ref}$, which may be stored in the memory of the controller 110. During operation, the pressure is measured at the recovery time $t_1$ to determine a measured recovery pressure $P_{1, meas}$. The measured recovery pressure $P_{1, meas}$ may be compared with the reference recovery pressure $P_{1, ref}$ and when the difference between the reference recovery pressure and the measured recovery pressure (i.e., $P_{1, ref}-P_{1, meas}$) exceeds a predefined limit, a signal may be generated by the controller 110 and appropriate remedial action may be taken.

Figure 4:
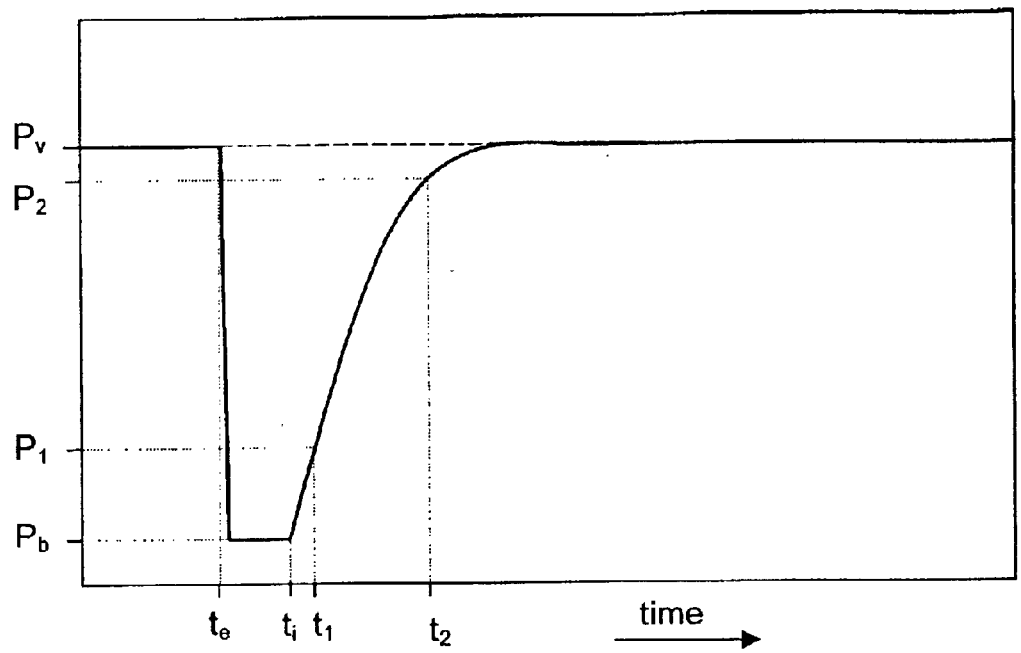
FIG. 4 is a pressure-time curve that illustrates a third arrangement for characterizing the partial pressure recovery of the source material in the source container.

FIG. 4 illustrates another modified arrangement for characterizing the pressure recovery. In this arrangement, the pressure rise $(P_2-P_1)$ is calculated between two predetermined times ($t_1$ and $t_2$). As with the previous arrangements, the pressure rise $(P_2-P_1)$ can be measured and compared to a reference value. If the difference between the measured pressure rise $(P_2-P_1)_{meas}$ and the reference value $(P_2-P_1)_{ref}$ is greater than a predetermined amount, the controller 110 may generate a signal so that appropriate remedial action may be taken.

Figure 5:
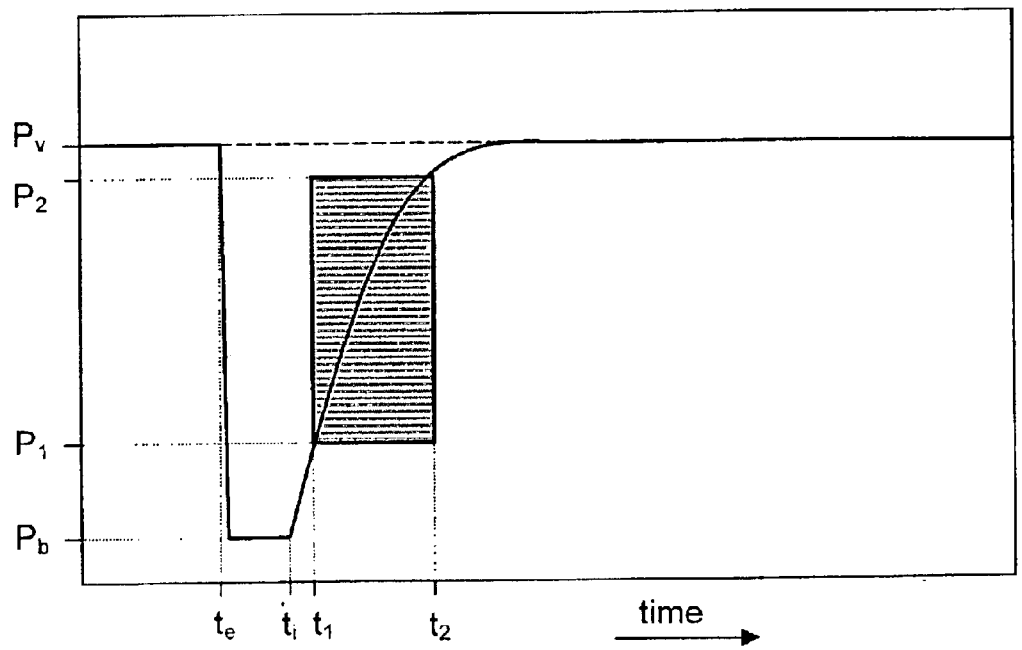
FIG. 5 is a pressure-time curve that illustrates a fourth arrangement for characterizing the partial pressure recovery of the source material in the source container.
Figure 6:
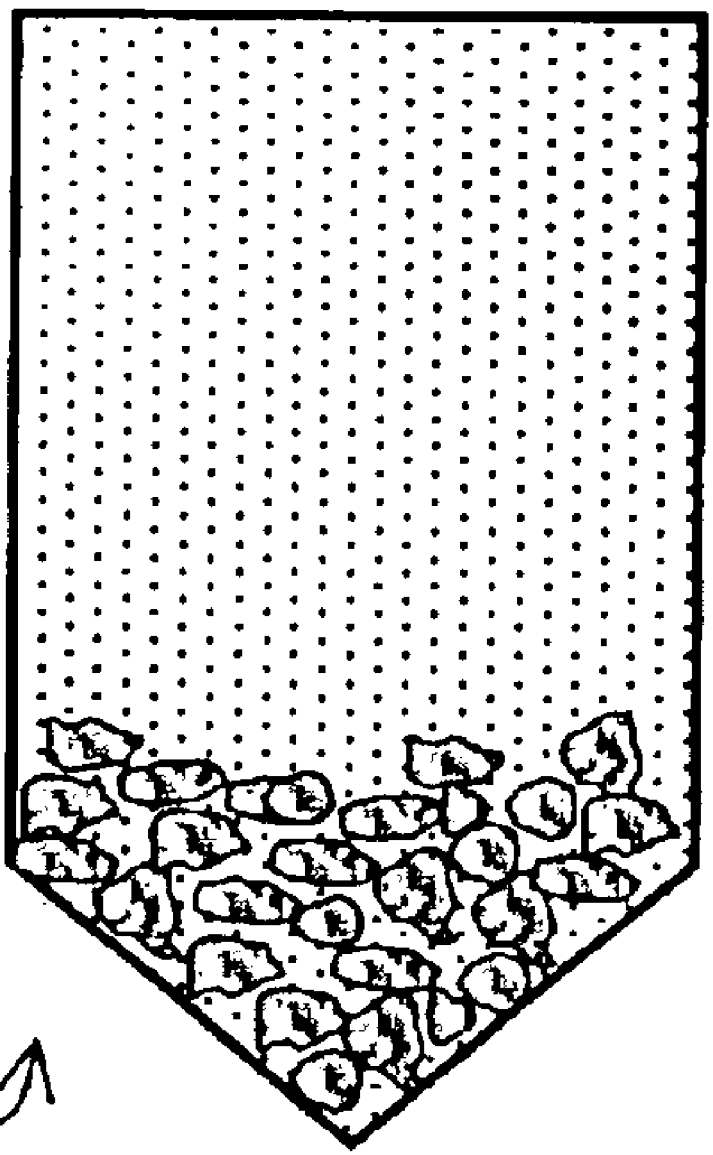
FIG. 6 is a schematic representation of a modified embodiment of a source container having certain features and advantages according to the present invention.

FIG. 5 illustrates another arrangement, wherein the pressure curve is monitored during a specified time interval between two predetermined times after isolation (i.e., $t_1$ and $t_2$) via a curve fitting method. Several different types of known curve fitting methods may be used, such as, for example, standard or non-linear curve fitting models, and typical shape function methodology (see e.g., U.S. Pat. No. 5,797,395 and the references identified therein, which are hereby incorporated by reference herein) The shape of a reference pressure curve may be determined under reference conditions for the specified time period. This reference is then compared to the measured shape of the pressure curve during the specified time periods. Significant changes in the shape of the pressure curve may trigger the controller 110 to sound an alarm. It should be appreciated that, although in both FIGS. 4 and 5, the first predetermined time $t_1$ is after the isolation time $t_i$, in a modified arrangement, the first specified time $t_1$ could coincide with the isolation time $t_i$.

It should be appreciated that the reference source container may be the same source container that is being used in the processing system. In such an arrangement, reference values are preferably determined at referenced conditions (e.g., a known amount and quality of source material). The reference values can be determined at the processing system 10 or at another location. In another arrangement, the reference container is not the same source container that is used in the processing system. For example, the reference container may be a standard container, which is representative of one type or style of source containers.

In another embodiment, the vaporized source material 104 is extracted from the source container 100 by purging an inert gas through the source container 100, preferably by placing the outlet end of the source container 100 in communication with a vacuum pump. The source container 100 is then isolated, leaving an amount of inert gas at an initial pressure $P_1$ inside the source container 100. After isolation, the recovery of the partial pressure of the vaporized source material is monitored by measuring a property that is indicative of the partial pressure as a function of time and compared with a reference property as a function time. In the illustrated arrangement, the property is the concentration of the vaporized source material in the source container 100. In such an arrangement, the sensor 112 is preferably configured as a concentration sensor, such as, for example, a spectrometer for measuring the absorption of electromagnetic radiation by the gas to be measured, a mass analyzer (e.g., a quadrupole mass analyzer), a time of flight mass analyzer or a magnetic field mass analyzer. Such concentration sensors can provide a signal that is proportional to the partial pressure of the vaporized source material in the source container 100.

In one embodiment, the controller 110 may be programmed to purge the source container 100 during a certain amount of time with an inert gas by opening the inert gas supply valve 137 and controlling the flow of inert gas with the mass flow controller 132. Preferably, the source container 100 is purged while the evacuation valve 146 to the pump 230 is opened and the isolation valve 144 is closed. After the source container 100 is evacuated, the inert gas supply valve 137 and the evacuation valve 146 are closed and the source container 100 is left isolated for a set time, while the controller 110 is configured to monitor the partial pressure recovery as a function of time with use of the source container sensor 112. The partial pressure as a function of time is then compared to a reference partial pressure as a function of time by the controller 110.

The measured partial pressure as a function of time can be characterized and compared to a reference partial pressure as described above with reference to FIGS. 2, 3, 4 and 5.

It should be noted that the methods described above do not directly measure the amount of source material 102 present in the source container 100. Rather, these methods measure the capability of the source material 102 in the source container 100 to produce vapor at a certain rate. As the source container 100 gets gradually depleted of source material 102, the free volume in the source container 100 will increase. When the production rate at which the vapor is produced remains constant, the pressure recovery after evacuation proceeds slower due to the increased volume to be filled with vapor. Further, due to a reduction of the evaporating surface area, crust formation, or other degradation of the source material, an additional reduction in pressure recovery rate may be observed. Consequently, with the methods described above a combination of conditions within the source container 100 is observed with each aspect being relevant to the capability of the source container 100 to deliver vaporized source material. The above described methods are, therefore, more relevant to the functioning of the processing system 10 than simply determining the amount of source material left in the source container 100, since it also accounts for vaporization indicating phenomena such as crust formation.

Under some conditions, the vapor production rate may remain initially at the desired value and then very suddenly drop to a low value due to a total depletion of source material. A sudden drop in the vapor production rate is especially undesirable if it occurs during a deposition process in the reaction chamber. As shown in FIG. 6, this situation can be prevented by giving the bottom of a source container 300 a non-flat shape, such as, for example, a conical or spherical shape. In the case of a liquid source material, the evaporating surface gradually decreases when the top level of the source material lies within the non-flat bottom of the source container 300. As such, the vapor production rate begins to drop and may be detected by the methods described above before total depletion of the source material. For a solid source material a non-flat bottom of the source container 300 is expected to have a similar effect Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

I claim:

1. A method for monitoring the capability of a liquid or solid source container to produce vaporized source material comprising:

reducing an amount of vaporized source material in the source container; isolating the source container;

measuring a property value that is indicative of partial pressure of the vaporized source material in the source container as a function of time;

comparing the measured property value as a function of time with a reference property value as a function of time; and generating a signal when the difference between the measured property value as a function of time and the reference property value as a function of time is larger than a predetermined value.

2. The method of claim 1 wherein reducing the amount of vaporized source material in the source container comprises evacuating the source container.

3. The method of claim 2 wherein measuring the property value that is indicative of the partial pressure of the vaporized source material as a function of time comprises measuring a pressure within the source container.

4. The method of claim 1 wherein reducing the amount of vaporized source material in the source container comprises purging the source container with an inert gas.

5. The method of claim 4 wherein measuring the property value that is indicative of the partial pressure of the vaporized source material as a function of time comprises measuring a concentration of the vaporized source material within the source container.

6. The method of claim 1 further comprising measuring the property value that is indicative of the partial pressure of the vaporized source material as a function of time in a reference source container to determine the reference property value as a function of time.

7. The method of claim 1 wherein measuring the property value that is indicative of partial pressure as a function of time, comparing the measured property value as a function of time, with the reference property value as a function of time and generating the signal comprise:

measuring a time period between isolating the source container and when the measured property value is within a predetermined range of property values;

comparing the measured time period with a reference time period taken between isolating a reference source container and the property value reaching the predetermined range of property values; and generating a signal when a difference between the measured time period and the reference time period exceeds a predetermined time.

8. The method of claim 7 wherein measuring the property value as a function of time comprises measuring a pressure within the source container as a function of time.

9. The method of claim 7 wherein measuring the property value as a function of time comprises measuring a concentration of the vaporized source material in the source container as a function of time.

10. The method of claim 1 wherein measuring the property value as a function of time, comparing the measured property value as a function of time, with the reference property value as a function of time and generating the signal comprise:

measuring the property value in the source container after a predetermined time period after isolating the source container;

comparing the measured property value after the predetermined time period with the reference property value measured after the predetermined time period after isolating a reference source container; and generating a signal when a difference between the measured property value after the predetermined time period and the reference property value after the predetermined time period exceeds a predetermined property value difference.

11. The method of claim 10 wherein measuring the property value as a function of time comprises measuring a pressure within the source container as a function of time.

12. The method of claim 10 wherein measuring the property value as a function of time comprises measuring a concentration of the vaporized source material in the source container as a function of time.

13. The method of claim 1 wherein measuring the property value as a function of time, comparing the measured property value as a function of time, with the reference property value of as a function of time and generating the signal comprise:

measuring the property value after a first time period after isolating the source container has elapsed;

measuring the property value after a second time period has elapsed;

comparing an increase in the measured property value between the first and second time periods to a reference increase in the property value between the first and second time periods in a reference container; and generating the signal when a difference between the increase in the measured property value and the reference increase in the reference property value in the reference container exceeds a predetermined property value difference limit.

14. The method of claim 13 wherein measuring the property value as a function of time comprises measuring a pressure within the source container as a function of time.

15. The method of claim 13 wherein measuring the property value as a function of time comprises measuring a concentration of the vaporized source material in the source container as a function of time.

16. The method of claim 1 wherein measuring the property value as a function of time, comparing the measured property value as a function of time, with the reference property value as a function of time and generating the signal comprise:

monitoring and characterizing a shape of the measured property value as a function of time between a first time period and a second time period;

comparing the shape of the measured property value as a function of time between the first time period and the second time period to a reference shape of the reference property value between the first time period and the second time period in a reference container; and generating the signal when a difference between the shape of the measured property value as a function of time and the reference shape of the reference property value amount as a function of time exceeds a predetermined shape difference limit.

17. The method of claim 1 further comprising providing an interior surface of the source container with a tapered bottom.

18. The method of claim 1 wherein the signal is an alarm.

19. The method of claim 1 wherein the signal is an automatic-shut off signal.

* * * * *